US00PP09806P

United States Patent [19]

van der Meer

[11] Patent Number: Plant 9,806

[45] Date of Patent: Feb. 18, 1997

[54] HYBRID TEA ROSE PLANT NAMED 'SELBARIUM'

[75] Inventor: Peter J. A. van der Meer, Uithoorn, Netherlands

[73] Assignee: Terra Nigra Holding B.V., De Kwakel, Netherlands

[21] Appl. No.: 591,389

[22] Filed: Jan. 25, 1996

[51] Int. Cl.[6] ..... A01H 5/00

[52] U.S. Cl. ..... Plt./11

[58] Field of Search ..... Plt./11, 18, 16

*Primary Examiner*—Howard J. Locker

[57] ABSTRACT

A new rose variety of the Hybrid Tea class, characterized by its continuous good production of large very soft pink with an orange blend flowers having a very good presentation, borne singly on upright stems on a bush of medium height (100–120 cm), and that is especially suitable for growing in Latin America considering the prevailing light intensity, day length and seasonal effects.

2 Drawing Sheets

BACKGROUND OF THE INVENTION

The present invention relates to a new and distinct variety of rose plant of the Hybrid Tea class, which was originated by me by crossing the unnamed seedling (Z37.116) with the unnamed seedling (SR 85.055).

The primary objective of this breeding was to obtain a new large type rose with a good presentation and bud shape in a trendy color having a high production. Among the novel characteristics possessed by the new variety which distinguish it from its parents and all other varieties of which I am aware are:

(1) A large flower and well shaped flower bud.

(2) The very soft pink color with an orange blend of the flower.

(3) Time of flowering is early to medium.

(4) Suitability for growing in Latin America.

(5) Rapid flowering cycles.

Asexual reproduction of the new rose variety by cutting and grafting using *R. canina* 'Inermis' as rootstock, as performed in a greenhouse in Quito, Ecuador, shows that the aforementioned characteristics and distinctions come true to form and are established and transmitted through succeeding propagations.

BRIEF DESCRIPTION OF THE DRAWINGS

The new variety of rose plant is illustrated by the accompanying photographic illustrations, of which:

Sheet 1 shows a full face view of the flower and

Sheet 2 shows typical specimens of the vegetative growth and flowers of the new variety in different stages of development and as depicted in color as nearly true as it reasonably possible to make the same in color illustrations of this character.

The following is a detailed description of this new variety, with color terminology in accordance with The Royal Horticultural Society Colour Chart (R.H.S.C.C.). The terminology used in the color description herein refers to plate numbers in the aforementioned color chart e.g. "55C" is plate "55C" of The Royal Horticultural Society Colour Chart.

Parentage: Seedling.

*Seed parent.*—Unnamed seedling Z37.116.

*Pollen parent.*—Unnamed seedling SR 85.055.

Classification:

*Commercial.*—Hybrid Tea.

BOTANICAL DESCRIPTION OF THE PLANT

Flower (Observations made from specimens grown in a greenhouse in Quito, Ecuador)

Blooming habit of 'Selbarium': Almost continuous.

Time of beginning of flowering: Early to medium.

A. Bud:

(1) *Size.*—Large. Diameter 4.0–4.5 cm. Length 5.5–6.0 cm.

(2) *Form.*—Egg shaped (long); is not affected by wet or hot weather.

(3) *Color.*—When the sepals first divide, the color of the outside is soft pink 20D.

(4) *Sepals.*—Length: 40 to 55 mm. Slightly branched, curl back when petals start to unfurl. Color: inside: 138B with striae in the middle of 138D. outside: 144A.

(5) *Calyx.*—Color: 144B. Shape: pear. Size: broad. Aspect: smooth. Odor when rubbed: a little.

(6) *Rate of opening.*—Slow to normal.

(7) *Peduncle.*—Length: medium, 7 to 8 cm. Aspect: covered with some tiny hairs. Strength: strong. Color: just below bloom 144A, lower 183A.

(8) *Opening.*—Opens up well; is not affected by adverse weather.

B. Bloom:

(1) *Size.*—Large; when fully expanded about 10 cm in diameter with a depth of about 5 cm.

(2) *Borne.*—Single.

(3) *Stems.*—Length: long. Strength: strong.

(4) *Form (when first open).*—Irregular round-shaped. Permanence: will flatten when aging.

(5) *Petalage.*—Number of petals: average 30.

(6) *Color.*—General coloration center of flower: in between 36A and 36B. Outer petals: generally between 27C and 27D. Inside of outer petals: base: 4D with a small spot at the base of 2D overlaid with 2B. middle zone: 27D flushed with 36C. marginal zone: 27D. Reverse of outer petals: base: 11D, other zones: 36D. General tonality: 36B washed with 27B.

(7) *Discoloration.*—General tonality 36B washed with 27B fading to in between 27B and 27C.

C. Petals:

(1) *Texture.*—Soft; is not affected by wet or hot weather.

(2) *Appearance.*—Inside: shiny. Outside: satiny.

(3) *Form.*—Obovate.
(4) *Arrangement.*—Regular.
(5) *Petaloids in center.*—Number: average 6. Size: 1 to 2 cm. Color: bottom 7A; top 36A.
(6) *Persistence.*—Drop off cleanly.
(7) *Fragrance.*—Absent.
(8) *Lasting quality.*—As cutflower: 10 days. On the plant: good.

Reproductive Organs

A. Stamens:
(1) *Arrangement.*—Regularly around styles.
(2) *Number.*—Average close to 300.
(3) *Length.*—11 to 16 mm.
(4) *Anthers.*—Size: medium, 3 to 4 mm. Color: 22A.
(5) *Filaments.*—Length: medium, 8 to 12 mm. Color: base of anthers 23B, lower filament 11B.
(6) *Pollen.*—Color: yellow.

B. Pistils:
(1) *Styles.*—Number: average close to 200. Length: large 8 to 12 mm. Color: Base: 154C. Top 38A spotted with 36A.
(2) *Stigmas.*—Color: 10A.
(3) *Fruit.*—Fertility: little. Fruit shape: pitcher-shaped.

Plant

A. Form: Greenhouse rose.
B. Growth: Upright to bushy.
C. Height: Medium, 100 to 120 cm.
D. Foliage: Compound of 1, 3, 5 or 7 leaflets. Average 8 to 10 compound leaves on bloom stem, 10 to 12 on main canes.
(1) *Size.*—Medium; 10 to 18 cm.
(2) *Quantity.*—Stem covering abundant.
(3) *Color.*—New foliage: upper side: 137A. under side: 138B. Old foliage: upper side: 141A. under side: 138B.
(3) *Texture.*—Upper side: leathery, glossy. Underside: leathery, dull.
(4) *Terminal leaflet.*—Shape: oval pointed, base rounded. Size: medium. Length 100 to 120 mm. Diameter 60 to 70 mm. Length petiole 20 to 25 mm.
(5) *Ribs and veins.*—Ordinary.
(6) *Rachis.*—Upper side: very few hairs and needles. Lower side: 2 to 3 mm sized hooked prickles, zero to 3 per compound leaf.
(7) *Margin type.*—Medium serrate, 2 to 3 points/cm, 2 to 3 mm peak.
(8) *Stipules.*—Length: average 20 to 25 mm, auricle to 5 to 7 mm. Texture: very few little hairs. Color: 144A.

E. Resistance to diseases: Average.
F. Wood:
(1) *New wood.*—Color: brownish; 183A. Bark: smooth.
(2) *Old wood.*—Color: green. Bark: smooth.

G. Thorns:
(1) *Quantity.*—Very few.
(2) *Form.*—Concave.
(3) *Length.*—8 to 10 mm.
(4) *Hooked.*—Little downwards.
(5) *Color (when young).*—Red-brownish; 185A.
(6) *Position.*—Irregular, low at flower stem.

H. Prickles:
*Quantity.*—On peduncle: none. On rachis: very few.

I. Short needles:
*Quantity.*—Very few on rachis.

I claim:

1. A new and distinct variety of rose plant of the Hybrid Tea class, substantially as herein shown and described characterized particularly as to novelty by its large soft pink with an orange blend flowers, borne singly on strong, upright stems with rapid growing cycles and especially suitable for growing in Latin America.

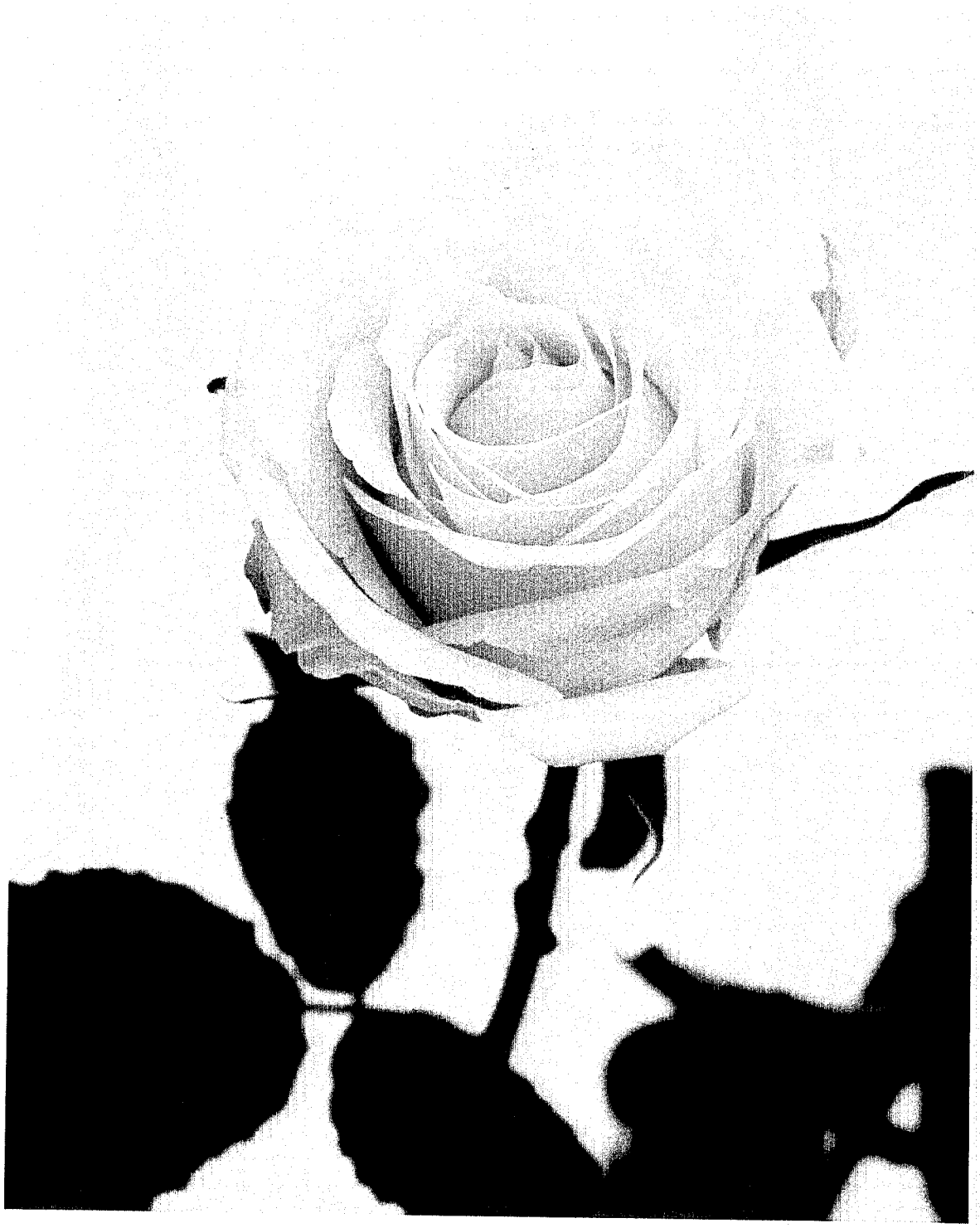

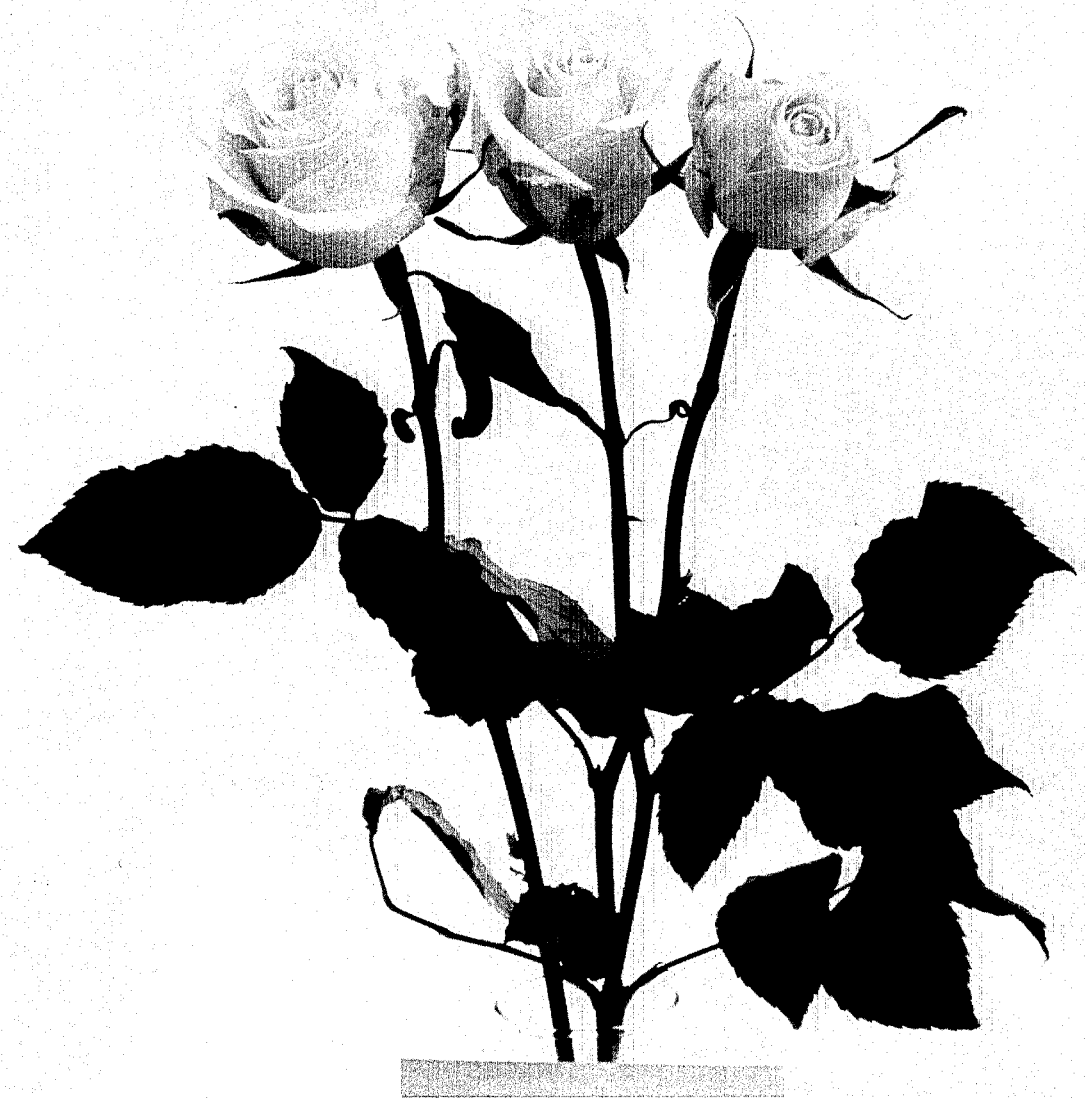

* * * * *